United States Patent [19]

Thomas et al.

[11] 4,112,952
[45] Sep. 12, 1978

[54] ELECTRODE FOR ARTIFICIAL PACEMAKER

[75] Inventors: George M. Thomas, Simpsonville; John W. Boretos, Rockville; Donald C. Syracuse, Bethesda, all of Md.; John A. Clark, Washington, D.C.; Anthony J. Vita, Mt. Airy; Vincent A. Gaudiani, Bethesda, both of Md.

[73] Assignee: The United States of America as represented by the Secretary of Health, Education and Welfare, Washington, D.C.

[21] Appl. No.: 767,996

[22] Filed: Feb. 11, 1977

[51] Int. Cl.² .................................... A61N 1/04
[52] U.S. Cl. .......................... 128/418; 128/419 P
[58] Field of Search ............. 128/404, 418, 419 P

[56] References Cited

U.S. PATENT DOCUMENTS

| 3,865,118 | 2/1975 | Bures | 128/404 |
| 3,866,615 | 2/1975 | Hewson | 128/404 X |
| 3,949,757 | 4/1976 | Sabel | 128/404 |
| 4,011,875 | 3/1977 | Lehr et al. | 128/418 |

FOREIGN PATENT DOCUMENTS

| 2,310,775 | 12/1976 | France | 128/404 |
| 2,124,684 | 11/1972 | Fed. Rep. of Germany | 128/418 |
| 246,004 | 6/1969 | U.S.S.R. | 128/419 P |

OTHER PUBLICATIONS

Porstmann et al., "P Wave Sychronus . . . Thoracotomy", The Am. J. Cardiology, v. 30, Jul. 1972, pp. 74–76.

*Primary Examiner*—Lee S. Cohen
*Attorney, Agent, or Firm*—John S. Roberts, Jr.; Norman J. Latker; Thomas G. Ferris

[57] ABSTRACT

An electrode for implantation in the heart to control atrio-ventricular block by artificial pacemaker including plural electrically conductive wires grouped in a bundle with spring metal arcuate prongs formed on one end thereof. A sheath is provided to compress the prongs for insertion of the electrode through a cannula to place the electrode against the heart. The electrode is implanted in the heart by advancing the prongs through the pericardium into the myocardium.

5 Claims, 13 Drawing Figures

ELECTRODE FOR ARTIFICIAL PACEMAKER

This invention relates generally to electrodes for implantation into body organs and more particularly to an electrode for artificial pacemakers for implantation into the heart muscle to stimulate heart activity.

Previous designs of pacemaker electrodes employ the use of a puncturing needle to penetrate the myocardium of the right ventricle. Electrodes are introduced through this needle and allowed to move about freely within the heart chamber making contact with the endocardium. Major risks are present, including electrode tip migration within the ventricular cavity, hemorrhage from cardiac puncture and thrombus formation on the wire.

The applicants are aware of the following U.S. Pat. Nos.

3,814,104 Irnich et al (June 4, 1974)
3,976,082 Schmitt (Aug. 24, 1976)
3,754,555 Schmitt (Aug. 28, 1973)
3,902,501 Citron et al (Sept. 2, 1975)
3,844,292 Bolduc (Oct. 29, 1974)

These systems are not comparable to the present invention in that they are transvenous electrodes and pace the endocardium. The "prongs" or tines of these devices are bulky and do not have the unique characteristics of the light spring spiral prongs of the present invention.

The following U.S. Pat. Nos. RE 27,569 Ackerman (Feb. 6, 1973) and 3,866,615 Hewson (Feb. 18, 1975), are illustrative of the above-mentioned prior art devices in which the electrode pierces the ventricle.

The U.S. Pat. No. to Quinn 3,416,534 (Dec. 17, 1968) discloses an electrode similar to that of the present invention in which a heavy, helical "cork-screw" type implantation device is provided to enter the myocardium. Aside from obvious disadvantages such, for example, as the inability to remove the electrode once it is implanted and the reliance on single electrode contact, the Quinn device cannot be controlled in depth of penetration of the electrode, thereby resulting in the danger of penetration of the ventricle with the dangers attendant thereon.

The present invention provides an electrode which does not enter the heart chamber but rather anchors securely within the myocardium itself. The invention provides an electrode in which positive fixation of the electrode tips is accomplished to prevent electrode tip migration. The configuration of the tips provided by the invention provides assurance of intimate electrical contact, avoiding the possibility of intermittent conductivity fluctuations. The nature and configuration of the electrode tip provides the lowest possible pacemaker's threshold due to the intimate contact provided thereby and the positive contact and increased electrode area presented by the multiple tips. By avoidance of penetration of the ventricle, the present invention precludes the risk of hemorrhage due to cardiac puncture and the thromboemboli which could be generated within the heart chamber by such penetration.

In a preferred embodiment the present invention provides an electrode for implantation in the myocardium to control atrioventricular block by artificial pacemaker, including a plurality of resilient electrically conductive wires grouped in coextensive parallel relationship in a bundle, means proximate one end of the bundle to fix the wires rotationally with respect to one another with the ends of the wire beyond the means deformed to describe arcuate pronged segments radiating from the axis of the bundle, insulation surrounding the bundle between the other ends of the wires and the means to fix the wires; and a tubular constraint removably disposable around the bundle to compress the prongs to the diameter of the bundle to permit insertion of the bundle through a cannula for subsequent expansion of the prongs and entry into the myocardium.

These and other advantages and objects of the invention will become better understood to those skilled in the art by reference to the following detailed description when viewed in light of the accompanying drawings wherein like components throughout the figures thereof are indicated by like numerals and wherein:

DESCRIPTION OF A PREFERRED EMBODIMENT

Figure 1:
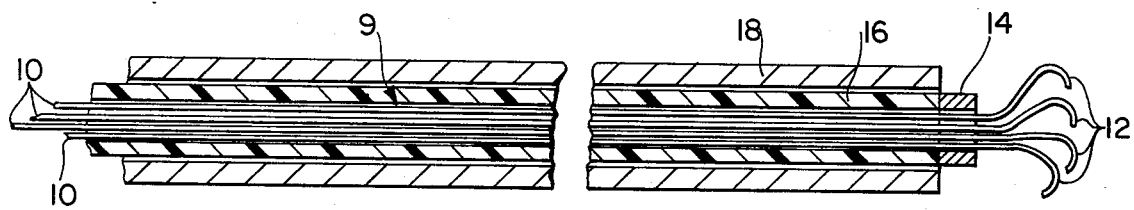
FIG. 1 is a sectional fragmentary view of an electrode in accordance with the invention in a first configuration of the device.

In FIG. 1 the device in accordance with the invention is shown in broken away section and consists of a bundle shown generally at 9 comprising four wires 10 disposed in parallel coextensive relationship to one another and having arcuate prongs 12 on one end thereof. The wires 10 are crimped together by a crimp 14 proximate the prongs 12 so that the prongs are fixed rotationally with respect to one another. The bundle 9 is completed by an insulated coating 16 formed around the wires 10 to electrically insulate them from their surroundings. The insulation 16 extends from the crimp 14 to the free ends of the wires 10. A tubular sheath 18 surrounds the bundle 9 for purposes to be described below.

The wires 10 are preferably made of a corrosion resistant alloy such, for example, as spring steel alloy manufactured under the trademark ELGILOY, now owned by American Gauge and Machine Company, Elgin, Illinois. ELGILOY is a spring steel first used in watches and clocks, now used in diverse applications and has the following composition: cobalt, 40%; chromium, 20%; nickel, 15%; molybdenum, 7%; manganese, 2%; carbon, 0.15%; beryllium, 0.04%; iron, 15.81%.

The wire strands 10 are thin, preferably on the order of 0.010 inch in diameter and are tempered to achieve a "spring effect" as will be described in detail below. The prongs 12 are preferably formed to describe the arc of a circle 5/32 inch in diameter and are approximately ½ inch in length and are bowed or curved in the same direction. The sheath 18 is preferably 18 gauge is size to fit over the resultant bundle 9. The thickness of the insulative coating 16 on the bundle of wires 10 is not in excess of 0.005 inch so that the final bundle assembly will slide freely within the 18 gauge tube.

The prongs 12, in the unconstrained configuration of FIG. 1, are disposed at approximately 90° to one another to radiate outwardly from the axis of the bundle 9 as shown.

Figure 2:
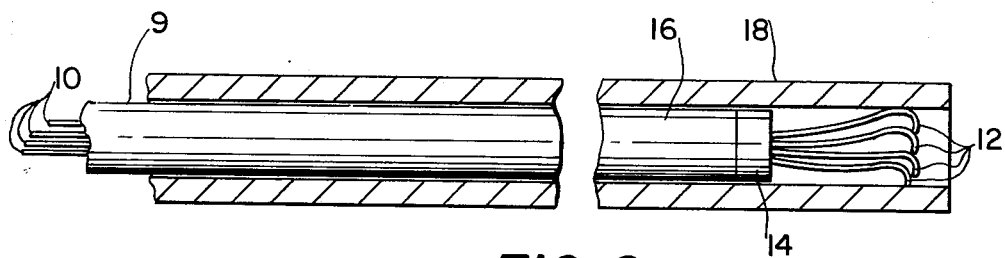
FIG. 2 is a view similar to FIG. 1 showing the electrode in another configuration.

By withdrawing the bundle 9 within the sheath 18 as shown in FIG. 2, it can be seen that the prongs are compressed to be constrained within the confines of the sheath 18 for purposes to be described below.

Figure 3:
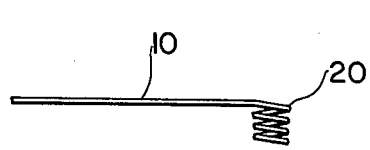
FIGS. 3-8 show various steps in the fabrication of an electrode in accordance with the invention.
Figure 4:
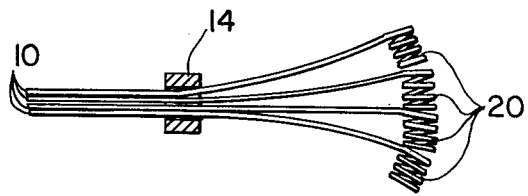
Figure 5:
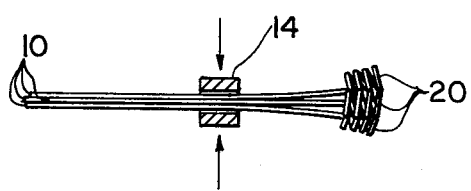
Figure 6:
Figure 7:
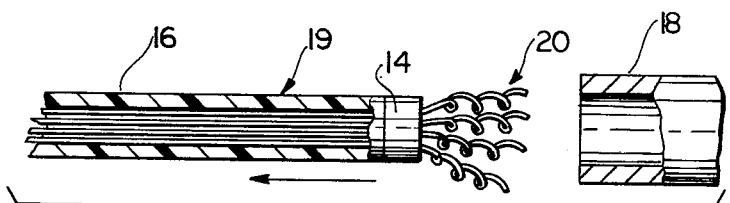
Figure 8:
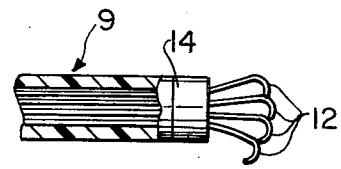

In FIGS. 3-8 one method involved in fabricating the electrode of FIGS. 1 and 2 is illustrated. In FIG. 3 an untempered ELGILOY wire 10 is coiled on one end with approximately four turns, forming a 5/32 inch diameter spring coil 20. Four wires with coils thus formed thereon are then inserted through a tubular crimp 14 of approximately 0.032 inch OD by 0.026 ID by 0.125 inch length as is shown in FIG. 4 and the crimp 14 is then compressed to fix the wires rotationally with respect to one another. In FIG. 5, the coils are bent at right angles to one another, forming a "four leaf clover" configuration as is best seen in the end view shown in FIG. 6. The assembly is then heat set at 410° C for 5 hours and cooled slowly to room temperature. The tempered wires are then passed through the 18 gauge sheath 18 as is shown in FIG. 7 to open the coils 20 to their final twisted shape as is seen in that figure. Each of the coils 20 are then cut to form the prongs 12 of approximately ½ inch in length. The entire bundle of wires 10 between the free end thereof and the crimp 14 is then coated with a dielectric insulating coating 16 of a suitable material such, for example, as polyurethane.

Figure 9:
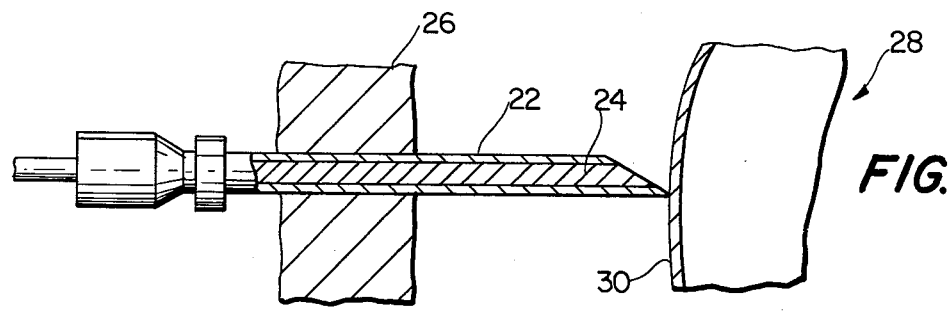
FIGS. 9-13 show various steps in the implantation of an electrode in accordance with the invention.
Figure 10:
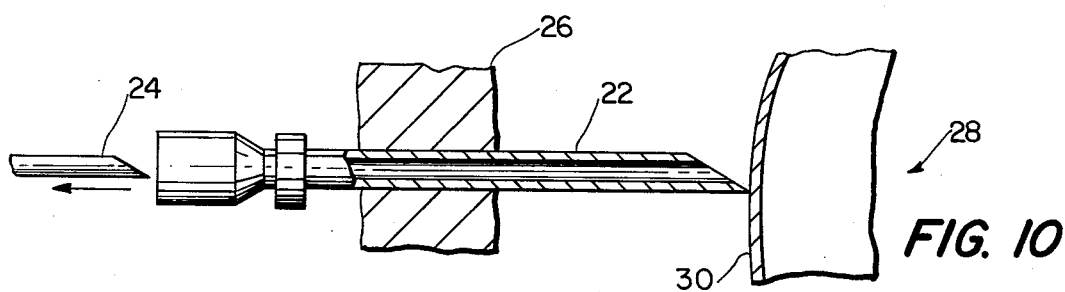
Figure 11:
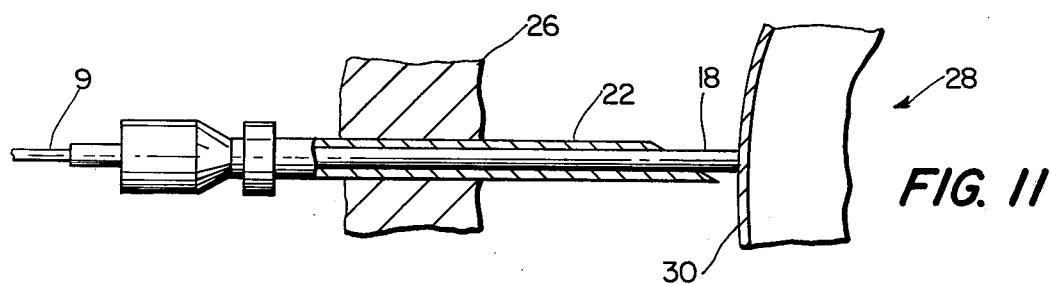
Figure 12:
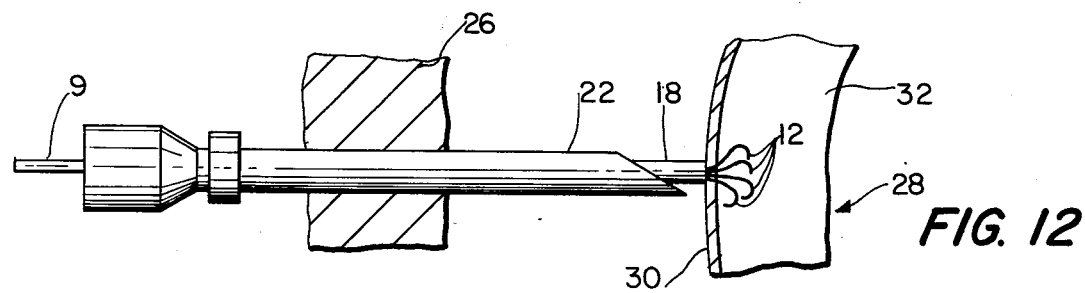
Figure 13:
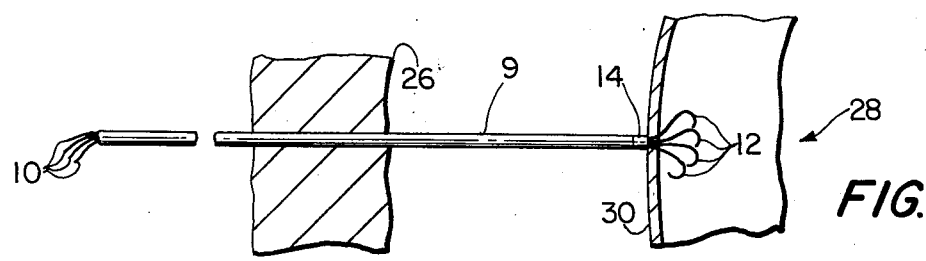

FIGS. 9-13 illustrate a use of the device in accordance with the invention. As shown in FIG. 9, implantation of the electrode is initiated by insertion of a 16 gauge cannula 22 with a trocar 24 through the chest wall 26 (5th intercostal space) toward the cardiac maximal impulse 28. When the chest wall is entered, the trocar 24 is removed, leaving the empty cannula 22 in the mediastinum as shown in FIG. 10, with the tip thereof resting against the pericardium 30 as seen in the figure. As seen in FIG. 11, the sheath 18 containing the bundle 9 in the configuration of FIG. 2 is then inserted through the cannula 22 with the end thereof resting against the pericardium. The bundle 9 is then advanced about 5 millimeters within the sheath 18 such that the electrode prongs 12 penetrate the pericardium into the myocardium 32 as is seen in FIG. 12. The cannula 22 and sheath 18 are then removed, leaving the electrode bundle 9 in the configuration of FIG. 13. The exterior ends of the wires 10 in the bundle are then connected to a conventional electronic pacemaker for stimulation of the heart in a manner well known in the art. Typically, an indifferent electrode, to complete the circuit, can be provided by a separate 2-0 steel suture (or other type) placed through the skin at the chest (not shown).

The utility of the invention has been demonstrated by 15 tests conducted on animals. Five animals underwent 50 repeated wire placements under direct vision through a left thorocotomy. The prongs were observed to advance, seek out, and embed in the myocardium without major difficulties. Pacing thresholds varied from 0.5-1.5 milliamperes, well within acceptable limits. Five animals were under 72 hour electrode implantation and removal with intermittent pacing. Intramyocardial position was confirmed by chest roentgenograms and electrocardiograms. Pacing thresholds were acceptable at an average level of 2.7 milliamperes. Five animals were continuously paced for 72 hours and exhibited a mean threshold of 2.9 milliamperes. Comparison of intermittent and continuous pacing showed that there was no significant difference.

An autopsy conducted on the animals revealed that all prongs were well embedded in the myocardium with minimal evidence of injury. The prongs coursed a plane 3 millimeters below the epicardium, providing a safety margin of 5-8 millimeters of myocardium from electrode intrusion into the heart chamber itself.

What has been described above is intended as exemplary to enable those skilled in the art in the practice of the invention.

What is new and desired to be protected by Letters Patent of the United States is:

1. An electrode for implantation in the myocardium to control atrio-ventricular block by artificial pacemaker comprising:
a plurality of resilient electrically conductive thin tempered wires grouped in coextensive, parallel relationship to form a bundle, means proximate one end of said bundle to fix said wires rotationally with respect to one another, the ends of said wires proximate said means being deformed to described arcuate segments radiating about the axis of said bundle to form prongs in the same direction and adapted to penetrate the pericardium to be implanted in the myocardium of the heart, insulation surrounding said bundle between said means and the ends of said wires remote from said means; and
constraining means associated with said prongs to compress them to the diameter of said bundle for insertion of said prongs through the chest wall and to remotely release them for penetration of the pericardium and implantation in the myocardium after movement of said prongs into the pericardium.

2. The electrode in accordance with claim 1 wherein said constraining means comprises a tubular sheath removably disposed around said bundle and compressing to compress said prongs to the diameter of said bundle.

3. The electrode in accordance with claim 1 wherein said wires comprise a spring steel alloy approximately 0.010 inch in diameter.

4. The electrode in accordance with claim 1 wherein said prongs are approximately ½ inch in length inscribing an arc of a circle of about 5/32 inch in diameter.

5. The electrode in accordance with claim 1 wherein four wires are grouped in said bundle and wherein said prongs are disposed in radial planes about 90° removed from one another.

* * * * *

UNITED STATES PATENT OFFICE
CERTIFICATE OF CORRECTION

Patent No. 4,112,952          Dated September 12, 1978

Inventor(s) George M. Thomas et al

It is certified that error appears in the above-identified patent and that said Letters Patent are hereby corrected as shown below:

Column 4, line 30, after "to form prongs" the word --bowed-- should be inserted.

Column 4, line 46, delete "to compress"

Signed and Sealed this

Second Day of January 1979

[SEAL]

Attest:

RUTH C. MASON
Attesting Officer

DONALD W. BANNER
Commissioner of Patents and Trademarks